(12) United States Patent
Field

(10) Patent No.: US 9,907,572 B2
(45) Date of Patent: Mar. 6, 2018

(54) SYRINGE ASSEMBLIES

(71) Applicant: The Cooper Companies Global Holdings LP, St. Michael (BB)

(72) Inventor: Stephen James Field, Kent (GB)

(73) Assignee: The Cooper Companies Global Holdings LP, St. Michael (BB)

( * ) Notice: Subject to any disclaimer, the term of this patent is extended or adjusted under 35 U.S.C. 154(b) by 107 days.

(21) Appl. No.: 15/037,730

(22) PCT Filed: Oct. 28, 2014

(86) PCT No.: PCT/GB2014/000434
§ 371 (c)(1),
(2) Date: May 19, 2016

(87) PCT Pub. No.: WO2015/079194
PCT Pub. Date: Jun. 4, 2015

(65) Prior Publication Data
US 2016/0302828 A1    Oct. 20, 2016

(30) Foreign Application Priority Data
Nov. 29, 2013    (GB) .................................. 1321078.6

(51) Int. Cl.
*A61B 17/435*    (2006.01)
*A61M 5/31*    (2006.01)
*A61M 5/315*    (2006.01)

(52) U.S. Cl.
CPC ......... *A61B 17/435* (2013.01); *A61M 5/3148* (2013.01); *A61M 5/31581* (2013.01)

(58) Field of Classification Search
CPC ..... A61B 17/425; A61B 17/43; A61B 17/435; A61M 5/3148; A61M 5/31581; A61M 2005/3152
See application file for complete search history.

(56) References Cited

U.S. PATENT DOCUMENTS

| 5,582,595 A | 12/1996 | Haber et al. |
| 2006/0217670 A1 | 9/2006 | Cecchi et al. |
| 2009/0308895 A1 | 12/2009 | Reynolds et al. |
| 2010/0305501 A1* | 12/2010 | Ratjen ................ A61M 5/2448 604/82 |
| 2014/0207082 A1 | 7/2014 | Lee |

FOREIGN PATENT DOCUMENTS

| WO | WO 97/028834 | 8/1997 |
| WO | WO 2007/092929 | 8/2007 |
| WO | WO 2013/005881 | 1/2013 |

OTHER PUBLICATIONS

PCT International Search Report (PCT/ISA/210) and Written Opinion (PCT/ISA/237) ISA/EP, PCT/GB2014/000434, dated Jan. 29, 2015.

* cited by examiner

*Primary Examiner* — Charles A Marmor, II
*Assistant Examiner* — Carrie R Dorna
(74) *Attorney, Agent, or Firm* — Fish & Richardson P.C.

(57) ABSTRACT

An embryo transfer syringe has a roller (30) coupled with the rear end of its plunger (15). The roller (30) is displaceable along an elongate housing (20) extending from the rear of the barrel (10) of the syringe. The roller (30) can be manually engaged through a slot (23) along the housing (20) to rotate it and roll it along the housing thereby smoothly and controllably displacing the plunger (15).

5 Claims, 2 Drawing Sheets

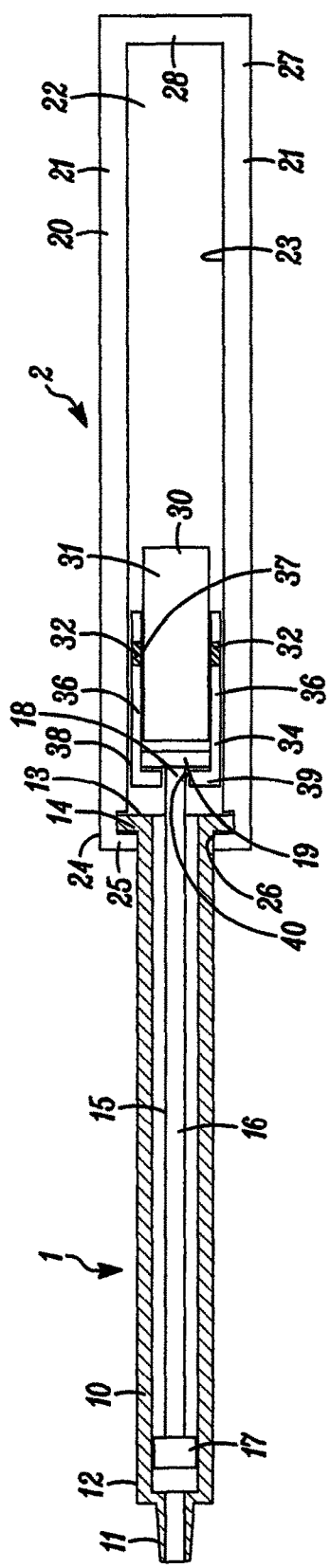

SYRINGE ASSEMBLIES

This invention relates to syringe assemblies of the kind including a barrel open at a forward end and a plunger movable along the barrel and having a rear end extending out of the opposite end of the barrel so that material can be aspirated into or dispensed from the barrel via its forward end.

The invention is more particularly, but not exclusively, concerned with embryo transfer syringes.

Embryo transfer syringes are used during assisted fertilisation procedures to withdraw an embryo from an in vitro or in vivo location and transfer it to a different location. It is of particular importance in maintaining the viability of the embryo that it is not subject to physical shock such as caused by sudden movement or harsh handling. The small size of such syringes can make them difficult to handle and operate in a smooth manner. It would be desirable, therefore, for an embryo transfer syringe to be capable of smooth, controlled operation using a single hand. There are also other medico-surgical procedures where it would be desirable to use a syringe that can be operated in a smooth manner.

It is an object of the present invention to provide an alternative syringe assembly.

According to one aspect of the present invention there is provided a syringe assembly of the above-specified kind, characterised in that the assembly includes an elongate housing extending from the rear end of the barrel, that the housing has an elongate opening extending along its length and a carriage displaceable along the housing, that the carriage has a portion that is accessible through the elongate opening, and that the carriage is coupled with the rear end of the plunger such that the plunger is moved along the barrel by manual displacement of the carriage.

The carriage may include a roller of circular section having an axis extending at right angles to the housing and having an edge accessible through the elongate opening on one side, the roller engaging an elongate part of the housing extending along its length such that the roller can be rotated and rolled along the length of the housing by manual engagement to displace the plunger along the barrel. The elongate part of the housing may be a floor of the housing, the edge of the roller engaging the floor of the housing. Alternatively, the housing may have a rail extending along its length, the roller having an axle that engages the rail. The rail may be provided with teeth, the axle of the roller being provided with splines that mesh with the teeth on the roller. The carriage may be separate from and be fastened with the rear end of the barrel. The syringe may be an embryo transfer syringe assembly.

According to another aspect of the present invention there is provided a syringe actuation sub-assembly including an elongate housing having a first end arranged to be fastened to the rear end of a syringe barrel, a carriage displaceable along the length of the housing that is accessible manually from outside the housing, the carriage being arranged to be fastened to the rear end of a syringe plunger such that the plunger can be displaced along the barrel by manually accessing the carriage and displacing the carriage along the housing.

The carriage preferably includes a roller of circular section having an axis extending at right angles to the housing and having an edge accessible through an elongate opening along the housing, the roller engaging an elongate part of the housing extending along its length such that the roller can be rotated and rolled along the length of the housing by manual engagement to displace the plunger along the barrel.

A syringe assembly and a syringe actuation sub-assembly according to the present invention will now be described, by way of example, with reference to the accompanying drawings, in which:

FIG. 1 is a plan view of the assembly;

FIG. 2 is a partly cut-away side elevation view of a part of the assembly;

Figure 3:
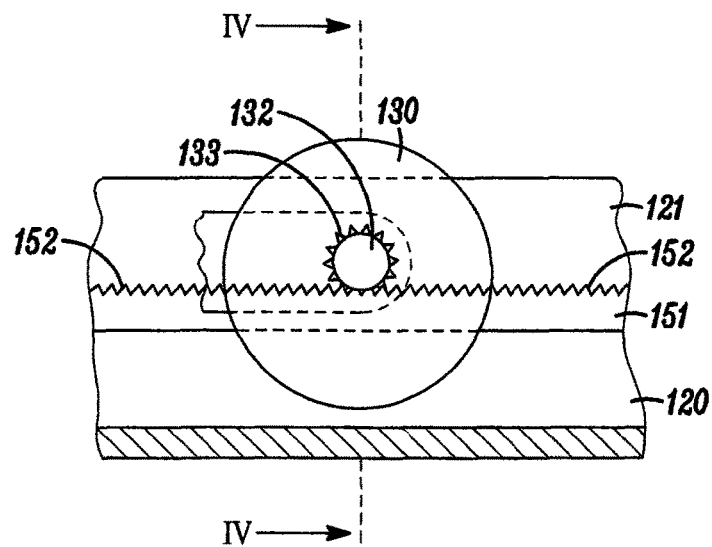
FIG. 3 is a cut-away side elevation view of a part of an alternative arrangement.

With reference first to FIGS. 1 and 2, the syringe assembly comprises a conventional syringe 1 attached at its rear end with a syringe actuation sub-assembly 2.

The syringe 1 is of the kind conventionally used in embryo transfer procedures and typically has a volume of about 1 to 5 ml, preferably 1 ml. The syringe 1 has a graduated barrel 10 with a nose 11 at its forward end 12 and an open rear end 13 having a narrow, radially-extending flange 14. The barrel 10 of the syringe 1 contains a plunger 15 comprising an axially-extending rod 16 with a wiper seal 17 at its forward end that contacts and seals with the inside of the barrel as the plunger is moved along it. The wiper seal could be an integral part of the plunger. The rear end 18 of the plunger 15 projects from the rear, open end 13 of the barrel 10 and is terminated by a radially-extending, circular thumb plate 19.

The actuation sub-assembly 2 is clipped onto the rear of the syringe 1. The sub-assembly 2 includes an outer housing 20 of generally rectangular, elongate shape and of approximately the same length as the barrel 10 of the syringe 1. The housing 20 includes a pair of parallel side walls 21 separated from each other along the lower side of the housing by a floor 22. The upper side of the housing 20 is open, defining an opening or slot 23 extending along its length. At its forward end 24 the housing 20 has an end wall 25 formed with an opening 26 of part circular, C-shape and with a diameter matched with the external diameter of the barrel 10. The barrel 10 of the syringe 1 is clipped into the opening 26 with the rear face of the end wall 25 in contact with the forward face of the flange 14. At its opposite, rear end 27 the housing 20 is closed by a transverse rear end wall 28. The housing 20 can be moulded as a single part of a stiff plastics material.

The sub-assembly 2 also includes a carriage in the form of a moulded plastics roller or wheel 30 of circular shape and with a flat peripheral edge 31. The roller 30 is located in the housing 20 between the side walls 21 so that its plane is aligned with the length of the housing and its axis of rotation is at right angles to the length of the housing. The roller 30 has two short stub axles 32 projecting outwards centrally on opposite sides. The width of the roller 30 including the axles 32 is slightly less than the width between the inside of the side walls 21 so that it can be moved freely along the housing 20. The diameter of the roller 30 is slightly greater than the internal depth of the housing 20 so that, when the edge 31 of the roller 30 at its lower side is in contact with the floor 22 of the housing 20, the upper side of the roller projects above the upper edge of the housing. In this way, the exposed edge 31 of the roller 30 is accessible along the length of the slot 23. Alternatively, the edge of the roller could be level with or slightly below the upper edge of the housing providing the width of the slot enabled the roller to be contacted and engaged by a finger or thumb. The roller 30 is attached with the rear end of the plunger 15 in some way.

As shown, the sub-assembly 2 includes a frame 34 having a pair of parallel side arms 36 extending longitudinally of the housing 20 on either sides of the roller 30, between the roller and the inside of the side walls 21. The stub axles 32 on the roller 30 project into and are journalled in mounting apertures 37 in each arm 36. The forward end 38 of the arms 36 are joined by a lateral bridge piece 39, which has a C-shape opening 40 into which the rear end of the plunger 15 is fitted, just forwardly of the thumb plate 19. In this way, the roller 30 is joined with the plunger 15.

The plunger 15 can be moved rearwardly along the barrel 10, to aspirate an embryo from an in vitro or in vivo location, simply by gripping the assembly in one hand, placing the thumb on the exposed edge 31 of the roller 30 and rolling it rearwardly along the housing 20. The dimensions of the housing 20 and the roller are such as to allow the plunger 15 to be displaced along the entire length of the barrel 10. Typically, the syringe assembly would be gripped like a tennis racquet or foil, with the sub-assembly 2 held between the forefinger and thumb and with the barrel 10 of the syringe 1 supported between the other three fingers and the palm of the hand. To dispense the contents of the syringe 1 the user simply uses his thumb to roll the roller 30 forwardly along the housing 20 and push the plunger 15 forwardly along the barrel 10. It will be appreciated that this rolling action to aspirate or dispense material can be accomplished in a very smooth and controlled manner compared with the conventional syringes where the plunger has to be pushed or pulled directly along the barrel. The syringe assembly of the present invention can also be used easily single-handed.

In the arrangement described above the action of pushing or pulling the roller 30 along the housing 20 applies a downward force as well as a force along the housing. This pushes the roller 30 against the floor 22 of the housing 20 and improves the frictional contact of its edge 31 with the floor. This frictional contact can be improved by appropriate choice of material of the housing and the roller. Alternatively, either the edge surface of the roller or the upper surface of the floor of the housing, or both, could be given an enhanced friction by means of a coating or a layer of a high-friction material. Instead of a simple frictional contact between the roller and the housing, the edge of the roller could be moulded with shallow ribs that engage similar ribs formed along the floor of the housing.

Figure 4:
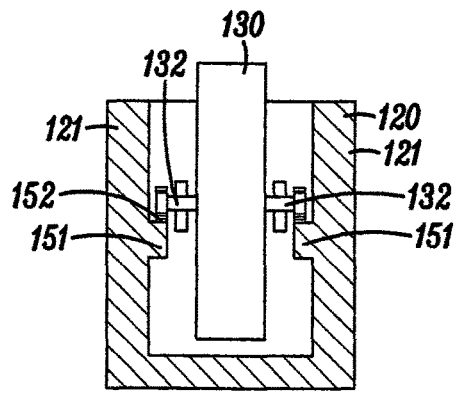
FIG. 4 is a transverse section along the line IV-IV of FIG. 3.
Figure 5:
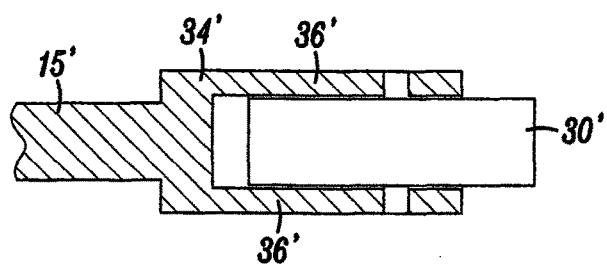
FIG. 5 is a plan view of a part of a plunger of another alternative syringe assembly.

Instead of rolling the roller by engagement with a floor of the housing the roller may engage an alternative part of the housing extending along its length. FIGS. 3 and 4 show an arrangement where the housing 120 has elongate rails 151 projecting on the inner surface of the two side walls 121 and extending parallel to the upper edge of the housing about half way up the height of the walls. The upper surface of the rails 151 is moulded with a toothed, rack profile 152. In this arrangement the outer end of the stub axles 132 is formed with splines 133 shaped to mesh and engage the teeth of the rack 152 on the rails. This arrangement, therefore, relies on mechanical engagement between the splines 133 and the rack 152 (instead of friction between the edge of the roller and a floor of the housing) to drive the roller along the housing as it is rotated. It will be appreciated that, in this arrangement, the housing need not have a floor, or the roller need not contact any floor.

The arrangement described above has the advantage of enabling a conventional syringe to be adapted by clipping on a separate actuation sub-assembly. Alternatively, the syringe itself could be specially provided such as by using a modified plunger 15', such as of the kind shown in FIG. 3 where the plunger is moulded with an integral frame 34' at its rear end with a pair of side arms 36' by which the roller 30' is supported.

In another possible arrangement, the syringe barrel and the roller housing could be moulded as a single part.

The manually-engageable carriage of the actuation sub-assembly need not be provided by a roller but could instead be a slider that was simply manually pushed along the housing. In such an arrangement, the friction between the slider and housing could be reduced by mounting the slider on a rail and, or alternatively, by using low friction material or lubrication on the contacting surfaces.

The invention is not confined to embryo transfer syringes but could be used in other syringes where it is important to be able to aspirate or dispense material in a controlled manner.

The invention claimed is:

1. A syringe assembly including a barrel open at a forward end and a plunger movable along the barrel and having a rear end extending out of an opposite rear end of the barrel so that material can be aspirated into or dispensed from the barrel via the forward end, the assembly including an elongate housing extending from the rear end of the barrel, the housing having an elongate opening extending along its length and a carriage displaceable along the housing, the carriage having a portion that is accessible through the elongate opening, and the carriage being coupled with the plunger such that the plunger is moved along the barrel by manual displacement of the carriage,
  wherein the carriage includes a roller having an axis extending substantially perpendicularly to the housing and having an edge accessible through the elongate opening, the roller having an axle that engages a rail that extends along a length of the housing such that the roller can be rotated and rolled along the length of the housing by manual engagement to displace the plunger along the barrel.

2. The syringe assembly of claim 1, wherein the rail is provided with teeth and that the roller is provided with splines that mesh with the teeth on the roller.

3. The syringe assembly of claim 1, wherein the carriage is separate from and is fastened with the rear end of the plunger.

4. The syringe assembly of claim 1, wherein the housing is separate from and is fastened with the rear end of the barrel.

5. The syringe assembly of claim 1, wherein the syringe assembly is an embryo transfer syringe assembly.

* * * * *